United States Patent [19]

Hang

[11] Patent Number: 4,791,058

[45] Date of Patent: Dec. 13, 1988

[54] GRAPE POMACE AS SUBSTRATE FOR MICROBIAL PRODUCTION OF CITRIC ACID

[75] Inventor: Yong D. Hang, Geneva, N.Y.

[73] Assignee: Cornell Research Foundation, Inc., Ithaca, N.Y.

[21] Appl. No.: 732,489

[22] Filed: May 10, 1985

[51] Int. Cl.$^4$ .......................... C12P 7/48; C12N 1/38; C12R 1/685

[52] U.S. Cl. .................................. 435/144; 435/244; 435/917; 426/52

[58] Field of Search ............... 435/144, 801, 917, 244; 426/49, 51, 52, 72

[56] References Cited

PUBLICATIONS

Hang et al., "Grape Pomace: A Novel Substrate for Microbial Production of Citric Acid"; *Biotechnology Letters*, vol. 7, No. 4, pp. 253–254 (Apr., 1985).

Hang et al., "Apple Pomace: A Potential Substrate for Citric Acid Production by *Aspergillus niger*"; *Biotechnology Letters*, 6 (11): 763–4 (Nov., 1984).

Rice, A. C.; "Solid Waste Generation and By-Product Recovery Potential from Winery Residues"; *Am. J. Enol Viticult.* 27 (1): 21–26 (1976).

Mekhtieva et al., "Saccharification of Grape Residue by Fungi"; *Biological Abstracts*, vol. 76, No. 10 (Nov. 15, 1983), abstract no: 71871.

Pouget et al., "Giving Value to Red Fruit Residues by Fermentation"; *Chemical Abstracts*, vol. 96, No. 11 (Mar. 15, 1982), abstract no. 84315z.

Moyer, A. J., "Effect of Alcohols on the Mycological Production of Citric Acid in Surface and Submerged Culture I. Nature of the Alcohol Effect"; *Applied Microbiology*, vol. 1, No. 1 (1953), pp. 1–7.

Moyer, A. J., "Effect of Alcohols on the Mycological Production of Citric Acid in Surface and Submerged Culture II Fermentation of Crude Carbohydrates"; *Applied Microbiology*, vol. 1, No. 1, (1953), pp. 7–13.

*Primary Examiner*—Elizabeth Weimar
*Attorney, Agent, or Firm*—Jones, Tullar & Cooper

[57] ABSTRACT

It has now been found that grape pomace can be employed as a substrate for citric acid production using *Aspergillus niger* as the fermentation agent.

4 Claims, 2 Drawing Sheets

GRAPE POMACE AS SUBSTRATE FOR MICROBIAL PRODUCTION OF CITRIC ACID

BACKGROUND OF THE INVENTION

Citric acid is widely used in the food and beverage industry, pharmaceutical industry and elsewhere. World-wide demand for this compound is in excess of 200,000 metric tons a year. Historically, and even today, the chief processes for the production of citric acid are microbial fermentation processes. A large number of organisms including fungi, yeast and bacteria have been examined as microbial agents to produce citric acid.

*Aspergillus niger* employed since the early part of this century is still apparently the organism of choice.

The basic methodology for citric acid production is throughly reviewed in "Prescott & Dunn's Industrial Microbiology" 4th Ed., 1982, Reed, edit., AVI Pub. Co., Inc., Westport, Conn., pps. 709-747 (hereby incorporated by reference).

Three principal methods of citric acid production by microbes are known: solid state culture, continuous culture and multi-stage fermentation processes. Most new technology is apparently based on submerged fermentation processes. The usual carbon sources are sucrose or molasses.

Where solid state fermentation has been employed the fermentation medium has been impregnated in porous solid materials such as sugarcane bagasse, potato or beet pulp, pineapple pulp and the like and then inoculated.

Grape pomace is the residue left from juice extraction and constitutes about 16% of the original fruit (*Rice, Am. J. Enol. Vitic.*, 27:21-26). In 1984, approximately 4.9 million metric tons of grapes were produced in the United States. Grape pomace is rich in carbohydrates, but its nitrogen and phosphorus contents are low (Rice, supra). At present, most pomace is dumped despite the increasing disposal problem posed and efforts made at by-product utilization (Famuyima and Ough, 1982, *Am. J. Enol. Vitic.*, 33:44-46).

DESCRIPTION OF THE INVENTION

Figure 1:
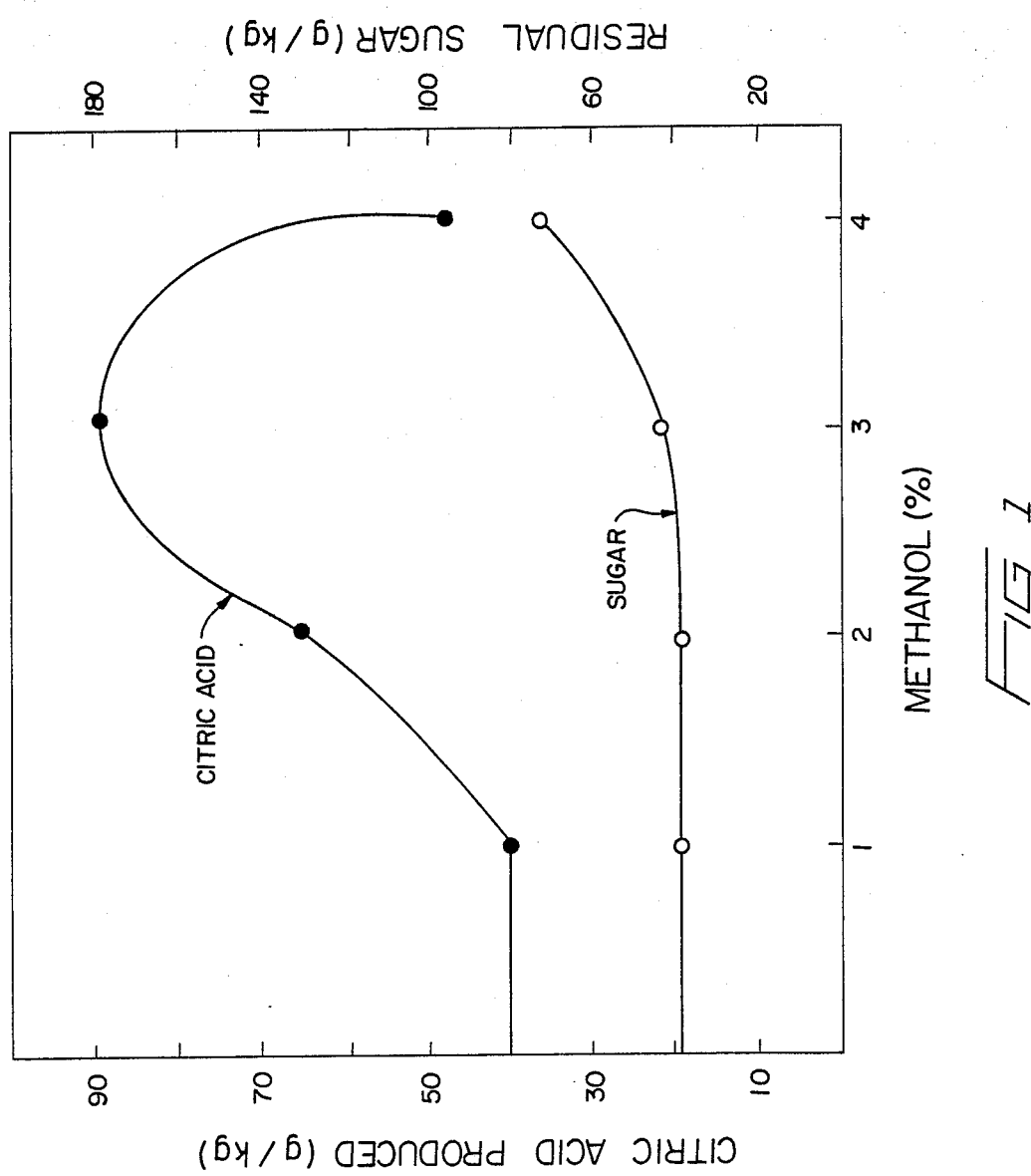
FIG. 1 is a plot of repetition of Example 5 varying the methanol content of the fermentation medium.

It has now been found that grape pomace can be employed as a substrate for citric acid production using *Aspergillus niger* as the fermentation agent. The grape pomace can be employed essentially as derived from the juice extraction process with the exception that it may be desirable to grind the pomace to an average particle size of about 0.25 inch or less to increase its surface area. This is surprising since the literature points out the yield of citric acid by microbial processes employing *A. niger* is susceptible to variations in pH, and in carbon, nitrogen, phosphate and sulfur content and source; and that yield is also governed by the presence of controlled amounts of trace elements such as bivalent iron, copper, zinc, manganese and magnesium ions.

The preferred process for producing citric acid using grape pomace as the substrate comprises a solid state culture fermentation wherein the grape pomace is mixed with a spore inoculum of citric acid producing *A. niger* in an amount sufficient to cause citric acid production, together with a citric acid production stimulating amount of methanol. The resultant mixture is fermented under solid state fermentation conditions at a pH, temperature and for a time sufficient to produce citric acid. The citric acid is then recovered, for example by recovery methods taught by *Prescott & Dunn's Industrial Microbiology*, supra.

Preferably the grape pomace has a sugar content between about 12 and about 22, in order to maximize citric acid production. Where the grape pomace has a relatively low sugar content sucrose or other appropriate carbon source can be added to the pomace before its use.

Preferably the pH of the grape pomace should be less than about 4.0. In the unlikely event the pH is higher it can be lowered using hydrochloric acid or sulphuric acid.

Preferably the moisture content of the pomace is at between about 75% and about 45%. When necessary the moisture content can be adjusted by hydration or dehydration.

As is conventional, to enhance citric acid production a simulation enhancing amount of methanol is added in the fermentation medium. Typically the amount of methanol added is an amount between about 1.0% volume and about 3.5% volume based on the weight of the grape pomace (i.e. c.c./100 grams).

The fermentation temperature is typically between about 25° C. and about 30° C. although slightly higher temperature can be employed.

Surprisingly for solid state culture, the time required for maximum citric acid production is about five days, whereas other fermentation processes have been reported to require 7 to 10 days.

The strain of *A. niger* employed in the process of this invention can be virtually any strain of citric acid producing *A. niger*. To date, *A. niger* NRRL 567 has produced the highest yield of citric acid. (NRRL 567 is also available from the ATCC as ATCC 12846).

There follows a number of examples which are to be considered illustrative rather than limiting. All parts and percentages are by weight and all temperatures are degrees centigrade unless otherwise specified.

EXAMPLES

Substrate: Grape pomace used in this study was obtained from the New York State Agricultural Experiment Station pilot plant juice processing unit located in Geneva, N. Y. and stored at −23° C. until needed. It contained 17.3% fermentable sugar as glucose and had a moisture content of 65.4%. The pH was 3.8.

Cultures: Five citric acid producing strains of *Aspergillus niger* were obtained from the ARS culture collection, Northern Regional Research Laboratory, U.S. Dept. of Agriculture, Peoria, Ill. Each culture was grown on a potato dextrose agar slant at 30° C. for 7 days. A spore inoculum was prepared by adding 3 ml of sterilized distilled water to each slant and shaking for one min.

Solid state fermentation: Portions of 40 g of grape pomace were introduced into 500 ml Erlemeyer flasks. Each flask was inoculated with an appropriate spore inoculum (about $1 \times 10^{-5}$ to about $1 \times 10^{-7}$ viable spores) and incubated at 30° C. for 4 days. Methanol was added to the flasks before fermentation. At the end of the fermentation, the fermented materials were extracted with water and the extracts were analyzed for residual sugar and citric acid.

Analytical methods: Sugar was determined as glucose by the phenolsulfuric acid method (Dubois et al., 1956, *Anal. Chem.*, 28350–356). Citric acid was measured by the colorimetric method of Taussky, 1949, *J. Biol. Chem.*, 181:195–198.

Results: Table 1 shows the production of citric acid from grape pomace by five strains of *Aspergillus niger*. The yields of citric acid varied and depended on (1) whether methanol was present in the substrate, and (2) the strain of *A. niger* used. Pomace samples fermented in the presence of methanol contained a much greater amount of citric acid than those fermented without the addition of methanol. The effect of methanol in increasing citric acid yields appears to be a general phenomenon in strains of *A. niger* and the use of methanol has become a common practice in citric acid production. Of the five cultures examined, *A. niger* NRRL 567 produced the greatest amount of citric acid from grape pomace in the presence of methanol at a concentration of 3% (volume/weight, i.e. c.c./100 grams) (Table 1). Based on the amount of sugar consumed, the average yield was 60%. *Prescott & Dunn's Industrial Microbiology*, supra, reported that the yield of citric acid from a sucrose or molasses medium impregnated in a carrier (sugarcane bagasse) by *A. niger* was 80%. Lakshminarayana et al, 1975, *Biotechnol. Bioeng.*, 17:291–293, reported that the yield of citric acid from a sugarcane molasses medium under solid state conditions in the presence of methanol was 58.7%.

TABLE 1

Citric acid production from grape pomace by *Aspergillus niger* (initial sugar content 173.4 g/kg)

| Example | Strain | Methanol % | Residual sugar g/kg | Yield of Citric Acid* g/kg sugar consumed |
|---|---|---|---|---|
| 1 | NRRL 2001 | 0 | 16.7 | 112 |
|   |           | 3 | 60.9 | 413 |
| 2 | NRRL 2270 | 0 | 14.4 | 160 |
|   |           | 3 | 23.6 | 511 |
| 3 | NRRL 599  | 0 | 21.9 | 304 |
|   |           | 3 | 60.0 | 498 |
| 4 | NRRL 328  | 0 | 14.5 | 170 |
|   |           | 3 | 30.0 | 523 |
| 5 | NRRL 567  | 0 | 19.1 | 275 |
|   |           | 3 | 19.8 | 600 |

*Yield based on an average of two runs

FIG. 1 shows results when Example 5 was repeated but varying the methanol content of the fermentation medium.

Figure 2:
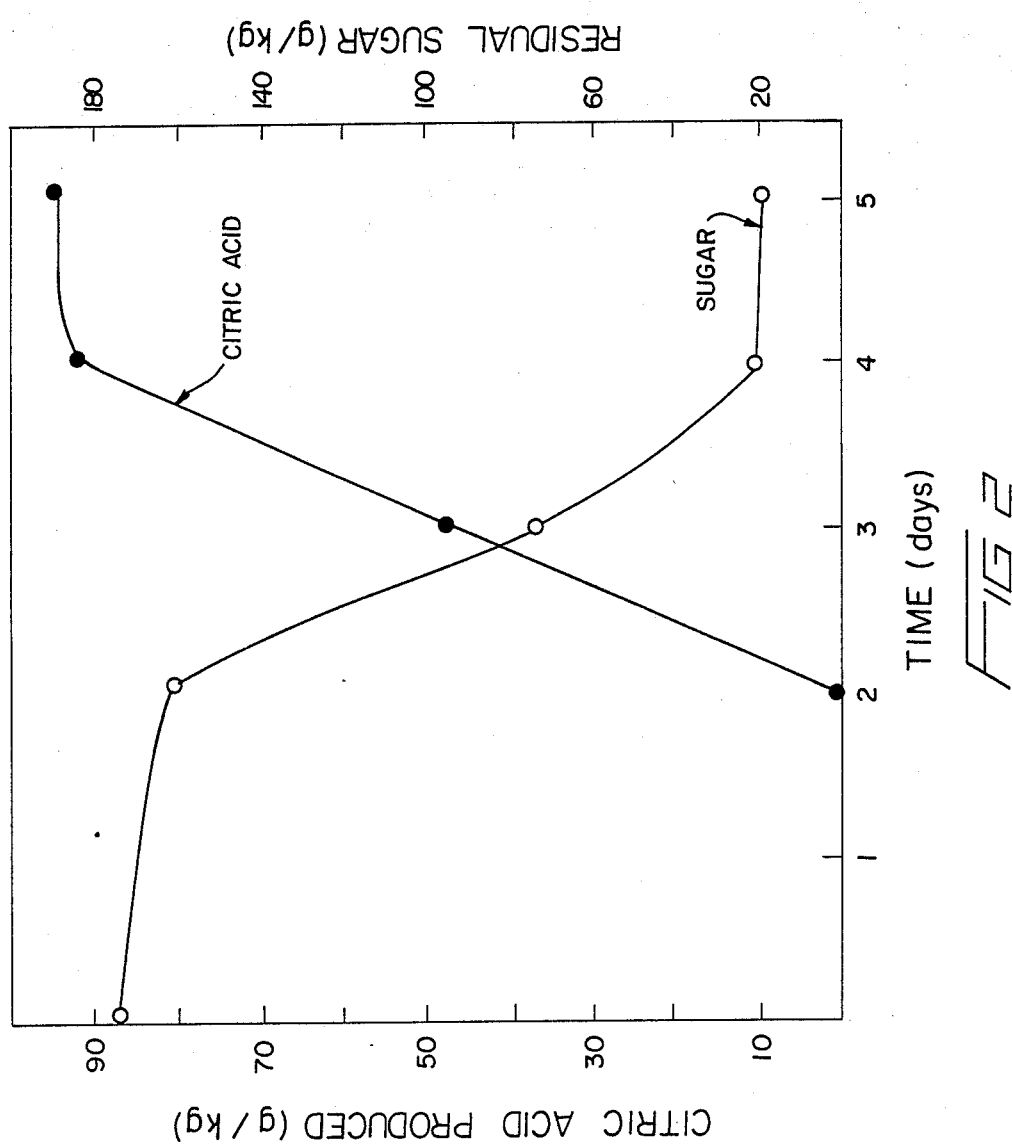
FIG. 2 is a plot of repetition of Example 5 varying the fermentation times.

FIG. 2 shows results when Example 5 was repeated for varying time intervals.

It should be understood that the invention can be practiced within the skill of the art in a manner other than that specifically exemplified above within the scope of the following claims.

I claim:

1. A fermentation process for producing citric acid which comprises fermenting grape pomace in the presence of citric acid producing amount of *Aspergillus niger* NRRL 567 in the presence of a citric acid production stimulating amount of methanol at a temperature and for a time sufficient to produce citric acid and recovering citric acid.

2. The process as in claim 1 wherein the fermentation process is a solid state fermentation process.

3. The process as in claim 1 which is conducted at a temperature between about 25° C. and about 30° C.

4. The process as in claim 1 wherein the amount of ethanol is between about 1.0 and about 3.5 volume based on the weight of the grape pomace.

* * * * *